United States Patent [19]

Bezwada et al.

[11] Patent Number: 5,713,920
[45] Date of Patent: Feb. 3, 1998

[54] ELASTOMERIC MEDICAL DEVICE

[75] Inventors: Rao S. Bezwada; Angelo G. Scopelianos, both of Whitehouse Station, N.J.

[73] Assignee: Ethicon, Inc., Sommerville, N.J.

[21] Appl. No.: 511,826

[22] Filed: Aug. 7, 1995

Related U.S. Application Data

[63] Continuation of Ser. No. 7,316, Jan. 21, 1993, Pat. No. 5,468,253.

[51] Int. Cl.$^6$ .................................................. C08G 63/82
[52] U.S. Cl. ........................ 606/230; 606/231; 528/357
[58] Field of Search ........................ 606/230, 76, 77, 606/219, 231; 528/357, 354

[56] References Cited

U.S. PATENT DOCUMENTS

| | | | |
|---|---|---|---|
| 4,045,418 | 8/1977 | Sinclair | 260/78.3 R |
| 4,057,537 | 11/1977 | Sinclair | 260/78.3 R |
| 4,243,775 | 1/1981 | Rosensaft | 525/415 |
| 4,429,080 | 1/1984 | Casey et al. | 525/415 |
| 4,605,730 | 8/1986 | Shalaby | 528/357 |
| 4,700,704 | 10/1987 | Jamiolkowski et al. | |
| 4,788,979 | 12/1988 | Jarrett et al. | 128/355.5 |
| 4,791,929 | 12/1988 | Jarrett et al. | 128/355.5 |
| 5,080,665 | 1/1992 | Jarrett et al. | 606/219 |
| 5,133,739 | 7/1992 | Bezwada et al. | 606/230 |
| 5,152,781 | 10/1992 | Tang et al. | 606/230 |
| 5,324,307 | 6/1994 | Jarrett et al. | 606/219 |
| 5,342,395 | 8/1994 | Jarrett et al. | 606/219 |
| 5,412,067 | 5/1995 | Shinoda et al. | 528/361 |
| 5,550,172 | 8/1996 | Regula et al. | 606/76 |

*Primary Examiner*—Michael Buiz
*Assistant Examiner*—Patrich W. Rasche
*Attorney, Agent, or Firm*—Hal Brent Woodrow

[57] ABSTRACT

Medical devices or components for medical devices formed from bioabsorbable elastomers comprising a random copolymer are disclosed. The random copolymer is a copolymer of from about 30 to about 70 weight percent of: a) ε-caprolactone, trimethylene carbonate, an ether lactone, or a mixture of these, and b) the balance being substantially glycolide, para-dioxanone, or a mixture of these. The random copolymers surprisingly exhibit elastomeric properties, and the copolymers are bioabsorbable. The combination of physical and biological properties of these elastomeric copolymers are particularly well-suited for numerous medical and surgical applications.

9 Claims, No Drawings

ELASTOMERIC MEDICAL DEVICE

This is a continuation of application Ser. No. 08/007,316, filed Jan. 21, 1993, now U.S. Pat. No. 5,468,253 which is hereby incorporated by reference.

BACKGROUND OF THE INVENTION

This invention relates to medical devices or components for such devices. More specifically, it relates to bioabsorbable elastomers fabricated into devices or components for devices suitable for medical applications.

The desirability of elastomeric materials for medical applications has been well established. For example, Thermoplast. Elastomers 3, Pap. Two-Day Semin., 3rd, pp. 68–71 (1991) discloses the fabrication of films and sheeting from copolyester elastomers for medical applications. These films can be used as transdermal patches for delivering bioactive agents through the surface of the skin, surgical wound dressings, I.V. site dressings, ostomy site dressings, and operating room garments. The copolyester elastomers are polymers with "hard" and "soft" segments. Their properties, such as flexibility, elasticity, and resistance to creep, can be tailored by varying the ratio of the hard and soft segments in the copolyester.

In addition to certain copolyesters which have elastomeric properties suitable for medical applications, polyurethane elastomers have also found acceptance within the medical community for numerous applications. This acceptance has led to the availability of Tecoflex® Aliphatic Polyurethanes for medical device applications. These elastomeric polyurethanes are prepared by reacting methylene bis(cyclohexyl) diisocyanate with poly(tetramethylene ether glycol). Some of the devices fabricated from these materials are intended primarily for implantation into the body. See the advertising brochure for TECOFLEX® Medical Grade Aliphatic Thermoplastic Polyurethanes from Thermedics, Inc.

While the commercial viability of elastomeric polymers for medical applications has been established, a need exists in the medical profession for certain properties which have not been met by the elastomeric polymers described above. For numerous applications, especially for those applications requiring a surgical device which is to be implanted in bodily tissue, the polymer from which the device is prepared must be bioabsorbable. In other words, the device must be capable of breaking down into small, non-toxic segments which can be metabolized or eliminated from the body without harm.

Unfortunately, although the elastomeric polymers described in the preceding references exhibit the requisite biocompatability, strength and processability, for numerous medical device applications, such elastomeric polymers are not absorbable in bodily tissue. Since these polymers are nonabsorbable in bodily tissue, surgical implants made from these elastomeric polymers would remain indefinitely within the bodily tissue, possibly causing adverse tissue reaction or other complications associated with the confinement of foreign matter in bodily tissue.

A large body of art has been created over many years, which focuses on the use of bioabsorbable polymers for numerous medical and surgical applications. As an example of this, the reader can review U.S. Pat. Nos. 5,133,739, 4,788,979 and 4,605,730. These patents teach the preparation of certain copolymer compositions of $\epsilon$-caprolactone and glycolide for specific bioabsorbable medical applications. The copolymer compositions are described as particularly useful for the preparation of filaments suitable for use as sutures, and for use as coating compositions for coating the surface of sutures to improve tiedown properties. Although the copolymer compositions described in these references exhibit a combination of outstanding biological and physical properties which make such polymer compositions particularly well adapted for numerous surgical applications, such polymer compositions do not exhibit a desirable degree of elasticity. Therefore, these copolymers would not be desirable for use in medical applications requiring elastomeric properties.

A partial answer to the problem of developing elastomeric copolymers which are biocompatible and bioabsorbable in bodily tissue has been suggested in the art. Griipma et al., Polymer Bulletin 25, 327–333 (1991), describes a 50/50 mole per mole copolymer of L-lactide and $\epsilon$-caprolactone. The copolymer is said to be elastomeric, and it degrades into non-toxic segments, so it is said to be useful for biomedical applications such as nerve guides. Similarly, U.S. Pat. Nos. 4,045,418 and 4,057,537 describe copolymers prepared from 75–85 parts by weight D,L-lactide and 25–15 parts of $\epsilon$-caprolactone. The copolymers are stated to be easily moldable, thermoplastic elastomers, which are biodegradable to harmless substances. Additionally, the copolymers can be modified by replacing a portion of the lactide with glycolide, and thus preparing a terpolymer of lactide/glycolide/$\epsilon$-caprolactone containing predominantly lactide.

While the elastomeric copolymers of lactide and $\epsilon$-caprolactone (optionally including glycolide) have addressed the needs for certain medical device applications, such copolymers have a major drawback which has prevented their widespread use. Although the copolymers can be literally interpreted to be "bioabsorbable", the rate of absorption is so slow that it renders the copolymers practically useless for numerous medical applications. This is so because the predominant component of the copolymer, which is polylactide, absorbs very slowly in bodily tissue. The other primary component of the copolymer, polycaprolactone, absorbs even slower. In addition, lactide polymerizes faster than $\epsilon$-caprolactone at 110° C. so that when the copolymer is made, a segmented copolymer containing long segments of polylactide spaced between segments of polycaprolactone is produced. The segmented structure of the copolymer further lowers its bioabsorption rate. All of these factors create a copolymer whose components and morphology do not lend themselves to acceptable bioabsorption rates for numerous medical applications.

In view of the deficiencies of the prior art, it would be highly desirable if medical devices or components for these devices could be fabricated from biocompatible polymers which exhibit the highly desired property of elasticity, without sacrificing mechanical properties, and yet also exhibit a rate of bioabsorbability which is fast enough for numerous medical device applications.

SUMMARY OF THE INVENTION

The invention is a medical device or part thereof formed from a bioabsorbable elastomer. The elastomer comprises a random copolymer of: a) from about 30 to about 50 weight percent of $\epsilon$-caprolactone, trimethylene carbonate, an ether lactone, or a mixture of any of $\epsilon$-caprolactone, trimethylene carbonate or an ether lactone, and b) the balance being substantially glycolide or para-dioxanone, or a mixture of glycolide and para-dioxanone.

Surprisingly, the random copolymer exhibits the properties of a bioabsorbable elastomer when it is processed to form a medical device or a component of a medical device.

This elastomer exhibits not only outstanding physical properties highly desired for elastomeric materials, but also bioabsorbability at a rate which accomplishes essentially complete bioabsorption within a reasonable time period. This is a necessary attribute for numerous medical applications. In preferred embodiments, the medical device or part of such device formed from the bioabsorbable elastomer has a high percent elongation, a low modulus, and outstanding tensile strength. These properties are achieved without sacrificing the bioabsorbability of the elastomeric polymer.

Unlike the elastomeric copolymers containing predominantly segments of polylactide, the random copolymers which form the medical devices of this invention exhibit a rate of bioabsorption which is fast enough for numerous medical applications. This is in contrast to the polylactide copolymers, which absorb at such a slow rate as to render them practically useless for a myriad of medical device applications.

The bioabsorbable elastomer can be formed into numerous medical and surgical devices, or components for such devices. For example, the elastomers can be fabricated to form elastomeric sutures, or as components of surgical clips and staples.

DETAILED DESCRIPTION OF THE INVENTION

For purposes of defining this invention, an "elastomer" is defined as a material which at room temperature can be stretched repeatedly to at least twice its original length and, upon immediate release of the stress, will return with force to its approximate original length. Preferably, the elastomer exhibits a high percent elongation and a low modulus, while possessing good tensile strength and good recovery characteristics. In the preferred embodiments of this invention, the elastomer from which the medical device or component of the device is formed exhibits a percent elongation greater than about 200, preferably greater than about 500. It will also exhibit a modulus (Young's Modulus) of less than about 40,000 psi, preferably less than about 20,000 psi. These properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch.

The term "bioabsorbable" is defined as those class of materials which readily react or enzymatically degrade upon exposure to bodily tissue for a relatively short period of time, thus experiencing a significant weight loss in that short period of time. Complete bioabsorption should take place within twelve months, although preferably bioabsorption will be complete within nine months and most preferably within six months. In this manner, the elastomer can be fabricated into medical and surgical devices which are useful for a vast array of applications requiring complete absorption within the relatively short time periods set forth in the preceding sentence.

The biological properties of the bioabsorbable elastomer used to form the device or part thereof, as measured by its absorption rate and its breaking strength retention in vivo (BSR), can be varied to suit the needs of the particular application for which the fabricated medical device or component is intended. This can be conveniently accomplished by varying the ratio of components of the elastomeric copolymer chosen.

The random copolymer which surprisingly exhibits the highly desired elastomeric properties can be prepared in accordance with the descriptions provided in U.S. Pat. Nos. 5,133,739 and 4,605,730, each of which is incorporated herein by reference, and with the experimental write-up provided in the Examples which follow. With respect to the teachings in these patents, each patent describes the preparation of a random copolymer of ε-caprolactone and glycolide, as an intermediate in the preparation of a crystalline segmented copolymer to be used for specific medical applications. It is the processing of this intermediate random copolymer which has led to the surprising discovery that the intermediate copolymer itself has the combination of outstanding properties, including its elastomeric properties, which make it well-suited for numerous medical applications.

The random copolymers are desirably prepared by reacting the monomers with an initiator such as a mono- or polyhydric alcohol, e.g. diethylene glycol, trimethylol propane, or pentaerythritol; or a hydroxy acid such as lactic or glycolic acid. Other initiators which can be used include polyalkylene glycols such as triethylene glycol, and polyhydroxy alkanes such as glycerol, mannitol, glucose, and the like.

The inherent viscosity of the random copolymer is desirably greater than about 0.6, preferably within a range of from about 1.0 to about 2.0, as measured in a 0.1 gram per deciliter (g/dL) solution of the polymer in hexafluoroisopropanol (HFIP) at 25° C. If the inherent viscosity is less than about 0.6 dl/g, then the strength properties of the copolymer would most likely be inadequate for numerous medical device applications. If the inherent viscosity were greater khan about 4.0 dl/g, then one may encounter significant processing difficulties in the fabrication of medical devices or components for such devices from the copolymers. This may require solution casting techniques to prepare useful products. In addition, the percent crystallinity of the random copolymer, as measured by x-ray diffraction, is advantageously less than about 25 percent, preferably less than about 15 percent. If the crystallinity of the copolymer were greater than about 25 percent, then the copolymer would be relatively stiff and non-elastomeric.

For purposes of defining the scope of this invention, the term "ether lactone" is meant to include 1,4-dioxepan-2-one, 1,5-dioxepan-2-one, substituted equivalents of these compounds, as well as the dimers of these compounds.

The preferred random copolymer is a copolymer of ε-caprolactone or trimethylene carbonate, and glycolide. The most preferred random copolymer is a copolymer of ε-caprolactone and glycolide. The amount of ε-caprolactone (or trimethylene carbonate, ether lactone, or a mixture of any of these with or without ε-caprolactone, if such equivalent components are used) from which the random copolymer is composed is critical to achieve acceptable elastomeric properties in combination with good mechanical properties. The preferred amount is between about 30 to about 50 weight percent. If less than 30 weight percent of ε-caprolactone is used, then the copolymer would not exhibit elastomeric properties. Additionally, it may be difficult to process such a copolymer by conventional techniques because such a copolymer may not be soluble in solvents traditionally used in medical applications. If the amount of ε-caprolactone in the random copolymer were greater than about 50 weight percent, then the strength properties of the copolymer would diminish appreciably, thus rendering the copolymer unsuitable for many applications where strength is needed, and the elastomeric properties would diminish as well. Preferably, the range of ε-caprolactone in the comonomer mixture from which the random copolymer is prepared ranges from about 30 to about 45 weight percent. Ideally, the range is from about 35 to about 45 weight percent.

Minor amounts of additives or comonomers can be added to the comonomer mixture from which the random copolymer is prepared, so long as these additional additives or comonomers do not significantly impact upon the elastomeric properties of the copolymers, or its rate of bioabsorption. For example, it may be desired to add certain components to modify or enhance the properties of the copolymer for specific applications. So long as the amount of ε-caprolactone in the comonomer mixture lies within the range from about 30 to about 50 weight percent, and the properties of the copolymer are not substantially effected, then such additional components may be used. Of course, the other primary component of the comonomer mixture in addition to ε-caprolactone is glycolide, para-dioxanone, or a mixture of these. Therefore, the term "substantially" which appears in the appended claims refers to allowing the incorporation of such minor components in addition to the balance of the copolymer composition being glycolide, para-dioxanone, or a mixture of these comonomers.

Surprisingly, the tensile properties of an ε-caprolactone/glycolide (PCL/PGA) 45/55 by weight copolymer which is initiated with trimethylol propane or pentaerythritol are enhanced considerably when compared to diethylene glycol initiated copolymer of the same composition.

Medical devices and components of these devices can be formed from the bioabsorbable elastomers described above using numerous techniques well known in the art. The elastomers can be melt-processed, for example by extrusion to prepare filaments or tubular structures. Alternatively, the copolymers can be injection molded to fabricate intricately designed parts, or compression molded to prepare films. For the details of such melt-processing techniques, see, for example, F. Rodriguez "Principles of Polymer Systems" McGraw Hill, 1970, Chapter 12.

The bioabsorbable elastomers can also be solvent cast to prepare thin films. Solvent casting can be accomplished using conventional methods such as first dissolving the copolymer in a suitable solvent to make a solution, then casting the solution on a glass plate to make a film, and then evaporating the solvent from the cast film. In another processing scheme, the copolymers can be lyophilized to prepare foams. Lyophilization can be accomplished by first dissolving the copolymer in an appropriate solvent, freezing the solution, and then removing the solvent under vacuum. The set of appropriate solvents include p-dioxane. Lyophilization techniques to prepare films are described in Aspects Theoriques Et Industriels De La Lyophilization by Louis Rey, 1964.

In a particularly preferred embodiment of this invention, tubular structures and films prepared from the elastomers are processed to provide orientation with respect to the polymer chains of the elastomeric copolymer. Uniaxial or biaxial orientation of the polymer chains of the copolymer in these tubular structures and films can be achieved by stretching. Although the stretching can be done at a variety of temperatures, it can generally be done at room temperature. Alternatively, films can be provided with radial orientation by compression molding.

Incorporating orientation into the bioabsorbable elastomers is highly desirable for certain medical devices because it improves the elasticity of such elastomers relative to those elastomers which do not have oriented chains. These improved properties are achieved without appreciably diminishing the outstanding strength properties of the copolymer, and consequently of the medical device derived from the copolymer. For a discussion on the preferred methods for providing orientation to tubular structures and films which would be applicable for the elastomers described here, see Extrusion and Other Plastics Operations, edited by N. M. Bikales, John Wiley & Sons (1971).

In another embodiment of this invention, the elastomers are reinforced with a filler Go improve desired properties. For example, the elastomers can be reinforced with absorbable fibers to prepare ultrasoft films which display high tear strength. The fibers may be desirably in the form of a knitted or non-woven mesh, for example Vicryl® (Polyglactin 910) knitted mesh.

The medical devices or components thereof envisioned within the scope of this application include ligating rubber bands for blood vessels, arteries, hemorrhoids, and other body components that need to be ligated; elastomeric sutures; highly flexible components of clips and staples; incorporation in blends for applications in devices needing improved hinge performance and toughness; films for drug delivery and adhesion prevention; gaskets; elastomeric coatings, and more specifically coatings for stents; elastomeric sealants; sleeves for anastomotic coupling devices; bioabsorbable vascular grafts; channels for nerve regeneration; wound dressings and adhesive strips; flexible meshes for numerous applications such as hernia repair; tubes for use as catheters and for the drainage of various body compartments and organs; plugs; tapes; pads; cords; contact lenses; or corneal bandage lenses. This listing is by no means completely exhaustive, and other devices which can be formed from the bioabsorbable elastomers described herein will readily be envisioned by one skilled in the art.

When the elastomer is reinforced with Vicryl® (Polyglactin 910) knitted mesh, the reinforced elastomer may be especially adapted for use as a pericardial patch or an adhesion prevention barrier in the form of a thin film.

The following examples illustrate the most preferred embodiments of this invention, and are intended to be merely illustrative without limiting the spirit and scope of the claimed invention.

EXAMPLE 1

COPOLYMER OF ε-CAPROLACTONE/ GLYCOLIDE AT 45/55 MOLE PERCENT

A flame dried 500 ml single-neck round-bottom flask is charged with 102.73 gm. (0.90 mole) of ε-caprolactone, 127.68 gm (1.10 mole) of glycolide, 0.228 ml (1.20 mmole/mole of total monomer) of distilled diethylene glycol and 0.135 ml stannous octoate (0.33 molar solution in toluene). The flask is fitted with a flame dried mechanical stirrer and appropriate adapters to provide a closed system. The reactor is purged three times before being vented with nitrogen. The reaction mixture is heated to 190° C. under nitrogen, and maintained at this temperature for about 16 to 18 hours. The copolymer is isolated, ground, and devolatilized (15 hours/110° C./0.1 mm Hg) to remove any unreacted monomers. A weight loss of 2.6% is observed. The inherent viscosity (I.V.) of the copolymer is 1.89 dl/g in hexafluoroisopropanol (HFIP) at 25° C. at 0.1 g/dl. The molar ratio of polycaprolactone(PCL)/polyglycolide(pGA) is found to be 44/56 by NMR. This copolymer has a glass transition temperature (Tg) of −11.9° C., and melting point of 51.9° C. by DSC.

PREPARATION OF FILMS

A vacuum compression molding machine is used to prepare at about 120° C. circular five inch diameter film samples with thicknesses of about 0.12 inch. The samples are cooled to ambient temperature under pressure, and kept inside a desiccator under nitrogen. ASTM Die C tensile specimens are prepared from the compression molded films.

The tensile properties of these five films, designated as Samples 1–5, are measured in accordance with ASTM D412, and the data is summarized in Table 1 below:

TABLE 1

Tensile Properties of Sample Films

| Sample Designation | Tensile Stress | | Elongation |
| --- | --- | --- | --- |
| | @ 300% Elong. [psi] | @ Break [psi] | @ Break [%] |
| 1 | 939 | 2057 | 745 |
| 2 | 496 | 1451 | 745 |
| 3 | 537 | 2084 | 950 |
| 4 | 548 | 1207 | 590 |
| 5 | 597 | 1591 | 615 |
| Average: | 623 | 1678 | 729 |
| Standard Deviation(S.D) | 180 | 384 | 143 |

As the data from Table 1 shows, the tensile properties are comparable to most commercially available elastomeric materials.

Tear resistance of the films is also tested according to ASTM D624. The sample did not tear at the junction, since there is no crack propagation. However the sample broke at about 290 lbs/inch with an extension up to 355%.

EXAMPLE 2

COPOLYMER OF ε-CAPROLACTONE/ GLYCOLIDE AT 40/60 MOLE PERCENT

The procedure described in Example 1 is substantially reproduced by reacting 91.3 gm (0.8 mole) of ε-caprolactone with 139.3 gm (1.2 mole) of glycolide. A weight loss of 1.1% is observed upon devolatilization. The I.V. of the copolymer is 1.83 dl/g in HFIP and the mole ratio of PCL/PGA is found to be 38.7/61.3 by NMR.

Preparation of foam by lyophilization

A 500 ml single-neck round-bottom flask equipped with a magnet stir bar is charged with 27.0 gms of 40/60 ε-caprolactone/glycolide copolymer and 243 ml of reagent 1,4-dioxane. The flask is fitted with a reflux condenser and nitrogen inlet and heated to reflux to dissolve the copolymer. The copolymer is completely dissolved in about three hours, and the resulting polymer solution is allowed to stir overnight under nitrogen at room temperature.

The polymer solution is pressure filtered through a 20 micron nylon mesh to remove any insoluble particulates and 162 grams of this filtered solution is poured into an eight inch silanized pyrex baking dish. The baking dish is covered with perforated aluminum foil and then transferred to a large capacity Virtis® lyophilizer, equipped with a Model No. 600 top freezing chamber, a 25SL bottom condenser unit and a secondary glass vacuum trap (with 45/55 joints) cooled by a dry ice/acetone dewar flask.

The dish containing the polymer solution is then frozen at a set temperature of −40° C. for 1 hour. The pressure in the freezing chamber is then reduced. After 0.25 hours at a pressure under 100 millitorr the set temperature of the freezing shelf is increased to −35° C. The freeze drying temperature/time scheme and resulting pressure readings are as follows:

| shelf temp. (°C.) | time (hrs) | final pressure reading (millitorr) |
| --- | --- | --- |
| −35 | 15.5 | 37 |
| −30 | 1.5 | 39 |
| −25 | 2.0 | 42 |
| −20 | 3.75 | |
| −10 | 16.75 | 52 |
| −5 | 4.0 | 52 |
| 0 | 3.75 | 52 |

At this stage the vacuum line is clamped off at a point just prior to the secondary trap. The vacuum pump is shut off and released to air, while the freezing chamber and the primary condensing trap remained under vacuum. The air-equilibrated secondary trap, which may be almost clogged, is then quickly replaced. The vacuum pump is then restarted. Once the pressure reading at the pump reached 50 millitorr, the chamber and primary trap are opened back up to full and continuous vacuum. The lyophilization continued as follows:

| shelf temp. (°C.) | time (hrs) | final pressure reading (millitorr) |
| --- | --- | --- |
| 5 | 64 | 58 |
| 20 | 2.75 | 58 |

The condensers and vacuum pump are then shut off and the unit is vented with nitrogen. The resulting foam is 3.2–4.0 mm thick, strong, soft and pliable. The NMR analysis indicate that the foam has no detectable level (>1000ppm) of 1,4 dioxane. The foam characteristics can be varied by changing the solution concentration and/or composition.

EXAMPLE 3

COPOLYMER OF ε-CAPROLACTONE/ GLYCOLIDE AT 50/50 MOLE PERCENT

The procedure described in Example 1 is substantially reproduced by reacting 114.14 gm (1.0 mole) of ε-caprolactone with 116.07 gm (1.0 mole) of glycolide. A weigh loss of 0.6% is observed upon devolatilization. The I.V. of the copolymer is 1.92 dl/g in HFIP and PCL/PGA molar ratio of 49.5/50.5 by NMR.

The tensile properties of the compression molded films of this elastomer are summarized below:

| | Tensile Stress | | Elongation |
| --- | --- | --- | --- |
| | @ 300% Elong. [psi] | @ Break [psi] | @ Break [%] |
| Avg. | 93 | 195 | 1307 |
| S.D. | 6 | 32 | 24 |

As illustrated from the data above, these films exhibit very high elongations, which are characteristic of desired thermoplastic elastomers.

EXAMPLE 4

COPOLYMER OF ε-CAPROLACTONE/ GLYCOLIDE AT 45/55 MOLE PERCENT

The procedure in Example 1 is substantially reproduced, except 0.22 gm of trimethylol propane (0.80 mmole/mole of total monomer) is used in place of diethylene glycol. A weight loss of 1.4% is observed when the polymer is devolatilized at 110° C. under high vacuum. The I.V. of the copolymer is 1.98 dl/g in HFIP and the mole ratio of PCL/PGA is found to be 43.8/56.2 by NMR. The glass transition temperature (Tg) and the melting point (Tm) of this copolymer are found to be −10° C. and 65° C., respectively, by DSC.

The tensile properties of the compression molded films of this elastomer are summarized below:

|  | Tensile Stress | | Elongation |
|---|---|---|---|
|  | @ 300% Elong. [psi] | @ Break [psi] | @ Break [%] |
| Avg. | 762 | 3664 | 1230 |
| S.D. | 144 | 379 | 27 |

As shown from the data above, this composition exhibits excellent tensile properties, and high elongation at break. The tensile properties are enhanced considerably with trimethylol propane as an initiator compared to diethylene glycol (see Example 1).

EXAMPLE 5

COPOLYMER OF ε-CAPROLACTONE/ GLYCOLIDE AT 45/55 MOLE PERCENT

The procedure in Example 1 is substantially reproduced, except 0.136 gm of pentaerythritol (0.50 mmole/mole of total monomer) is used as an initiator. A weight loss of 2.4% is observed when the polymer is develotalized at 110° C. under high vacuum. The I.V. of the copolymer is 1.96 dl/g in HFIP and the mole ratio of PCL/PGA is found to be 41.7/58.3 by NMR. The glass transition temperature (Tg) and the melting point (Tm) of this copolymer are found to be −8° C. and 64° C., respectively, by DSC.

The tensile properties of the compression molded films of this elastomer is summarized below:

|  | Tensile Stress | | Elongation |
|---|---|---|---|
|  | @ 300% Elong. [psi] | @ Break [psi] | @ Break [%] |
| Avg. | 842 | 3223 | 1143 |
| S.D. | 63 | 413 | 62 |

The tensile properties of this copolymer, which is initiated with pentaerythritol, are equivalent to trimethylolpropane initiated copolymer (Example 4) and better than diethylene glycol (Example 1). This copolymer exhibits excellent elastomeric properties compared to commercial non-absorbable elastomeric polyurethane (Tecoflex®).

EXAMPLE 6

COPOLYMER OF ε-CAPROLACTONE/ GLYCOLIDE AT 35/65 MOLE PERCENT

A flame dried 500 ml single-neck round-bottom flask is charged with 79.90 gm. (0.70 mole) of ε-caprolactone, 150.89 gm (1.30 mole) of glycolide, 0.228 ml (1.20 mmole/mole of total monomer) of distilled diethylene glycol and 0.135 ml stannous octoate (0.33 molar solution in toluene). The flask is fitted with a flame dried mechanical stirrer and appropriate adapters to provide a closed system. The reactor is purged three times before being vented with nitrogen. The reaction mixture is heated to 190° C. under nitrogen, and maintained at this temperature for about 16 to 18 hours. The copolymer is isolated, ground, and devolatilized (42 hours/ 110° C./0.1 mm Hg) to remove any unreacted monomers. A weight loss of 4.8% is observed upon devolatilization. The inherent viscosity (I.V.) of the copolymer is 1.46 dl/g in hexafluoroisoproponal (HFIP) at 25° C. The molar ratio of PCL/PGA is found to be 32.2/67.8 by NMR. The glass transition temperatures (Tg) and the melting point (Tm) of this copolymer are found to be 7° C./58° C. and 133° C., respectively, by DSC.

The tensile properties of the compression molded films of this elastomer are summarized below:

|  | Tensile Stress | | Elongation |
|---|---|---|---|
|  | 300% Elong. [psi] | @ Break [psi] | @ Break [%] |
| Avg. | 2350 | 4309 | 646 |
| S.D. | 73 | 985 | 133 |

By changing the composition of ε-caprolactone/glycolide from 45/55 to 35/65, the tensile strength is more than doubled while maintaining high elongations.

EXAMPLE 7

COPOLYMER OF ε-CAPROLACTONE/ GLYCOLIDE AT 40/60 MOLE PERCENT

The procedure described in Example 1 is substantially reproduced. A weight loss of 0.9% is observed upon devolatilization. The I.V. of the copolymer is 1.62 dl/g in HFIP and the mole ration of PCL/PGA is found to be 42.3/57.7 by NMR.

The tensile properties of the compression molded films of this elastomer are summarized below:

|  | Tensile Stress | | Elongation |
|---|---|---|---|
|  | @ 300% Elong. [psi] | @ Break [psi] | @ Break [%] |
| Avg. | 1145 | 4290 | 1151 |
| S.D. | 39 | 490 | 87 |
| In Vitro properties after 7 days/37° C./pH7.27 | | | |
| Avg. | — | 1213 | 217 |
| S.D. | — | 35 | 173 |

The tensile properties of this composition exhibited high tensile strength and high elongation at break, which are equivalent to many commercially available medical grade non-absorbable thermoplastic elastomers.

In Vitro properties are determined by measuring the tensile properties after the indicated number of days in a phosphate buffer with a pH of 7.27 at 37° C.

EXAMPLE 8

COPOLYMER OF ε-CAPROLACTONE/ GLYCOLIDE AT 45/55 MOLE PERCENT

The procedure in Example 1 is substantially reproduced. A weight loss of 0.8% is observed upon devolatilization. The I.V. of the copolymer is 1.49 dl/g in HFIP and the mole ratio of PCL/PGA is found to be 44.3/55.7 by NMR.

The tensile properties of the compression molded films of this elastomer is summarized below:

|  | Tensile Stress | | Elongation |
|---|---|---|---|
|  | @ 300% Elong. [psi] | @ Break [psi] | @ Break [%] |
| Avg. | 621 | 1802 | 993 |
| S.D. | 13 | 323 | 153 |
| In vitro properties after 7 days/37° C./pH7.27 | | | |
| Avg. | — | 477 | 169 |
| S.D. | — | 47 | 45 |

This composition also exhibits excellent elastomeric properties.

EXAMPLE 9

COPOLYMER OF TRIMETHYLENECARBONATE/GLYCOLIDE AT 45/55 MOLE PERCENT

A flame dried 250 ml single-neck round-bottom flask is charged with 45.94 gm. (0.45 mole) of trimethylenecarbonate, 63.84 gm (0.55 mole) of glycolide, 0.114 ml (1.20 mmole/mole of total monomer) of distilled diethylene glycol and 0.0673 ml stannous octoate (0.33 molar solution in toluene). The flask is fitted with a flame dried mechanical stirrer and appropriate adapters to provide a closed system. The reactor is purged three times before being vented with nitrogen. The reaction mixture is heated to 190° C. under nitrogen, and maintained at this temperature for about 16 to 18 hours. The copolymer is isolated, ground, and devolatilized (14 hours/110° C./0.1 mm Hg) to remove any unreacted monomers. A weight loss of 0.4% is observed upon devolatilization. The inherent viscosity (I.V.) of the copolymer is 1.16 dl/g in hexafluoroisoproponal (HFIP) at 25° C. The molar ratio of polytrimethylenecarbonate(PTMC)/PGA is found to be 44.9/55.1 by NMR. The glass transition temperature (Tg) of this copolymer is found to be 17° C. by DSC.

The tensile properties of the compression molded films of this elastomer are summarized below:

|  | Tensile Stress | | Elongation |
|---|---|---|---|
|  | @ 300% Elong. [psi] | @ Break [psi] | @ Break [%] |
| Avg. | 349 | 385 | 1272 |
| S.D. | 13 | 31 | 50 |

The films of this copolymer exhibit high elongations, characteristic of elastomeric materials.

EXAMPLE 10

COPOLYMER OF TRIMETHYLENECARBONATE/GLYCOLIDE AT 40/60 Mole %

The procedure described in Example 9 is substantially reproduced by reacting 41.15 gm.(0.40 mole) of trimethylenecarbonate, 69.64 gm. (0.60 mole) of glycolide. A weight loss of 0.4% is observed upon devolatilization. The I.V. of the copolymer is 1.19 dl/g in HFIP. The mole ratio of PTMC/PGA is found to be 39/61 by NMR. The Tg of this copolymer is found to be 18° C. by DSC.

The tensile properties of the compression molded films of this elastomer are summarized below:

|  | Tensile Stress | | Elongation |
|---|---|---|---|
|  | @ 300% Elong. [psi] | @ Break [psi] | @ Break [%] |
| Avg. | 472 | 1039 | 1168 |
| S.D. | 8 | 166 | 80 |

The films of this composition, PTMC/PGA at 40/60, exhibit high elongations, characteristic of elastomeric materials.

EXAMPLE 11

COPOLYMER OF TRIMETHYLENECARBONATE/GLYCOLIDE AT 30/70 Mole %

The procedure described in Example 9 is substantially reproduced by reacting 15.31 gm.(0.15 mole) of trimethylenecarbonate, 40.62 gm. (0.35 mole) of glycolide, 0.05695 ml (1.20 mmole/mole of total monomer) of distilled diethylene glycol and 0.03367 ml stannous octoate (0.33 molar solution in toluene). A weight loss of 0.6% is observed upon devolatiliztion. The I.V. of the copolymer is 1.13 dl/g in HFIP. The mole ratio of PTMC/PGA is found to be 29.7/70.3 by NMR. The Tg of this copolymer is found to be 24° C. by DSC.

The tensile properties of the compression molded films of this elastomer are summarized below:

|  | Tensile Stress | | Elongation |
|---|---|---|---|
|  | @ 300% Elong. [psi] | @ Break [psi] | @ Break [%] |
| Avg. | 994 | 1391 | 551 |
| S.D. | 115 | 113 | 85 |

The tensile properties of this copolymer are good and exhibit high elongations, a characteristic of elastomeric materials.

RECTANGULAR TORSION DATA OF ABSORBABLE ELASTOMERS

Several absorbable elastomers of varying compositions are tested using a Rheometrics RDA II Dynamic Mechanical Analyzer to study the effect of composition on tensile modulus (Modulus E'). Compression molded samples of 0.5"×1.5"×0.060" are used for the testing. Glass transition temperature (Tg) and small strain (0.5%) modulus are obtained. The torsion modulus is converted to tensile modulus using a Poisson's ratio of 0.5 as for an ideal rubber. Some of the data is summarized below:

| Example # | A | B | C | D | E | F |
|---|---|---|---|---|---|---|
| Composition, mole % | | | | | | |
| caprolactone | 45 | 40 | 50 | 45 | 45 | 35 |
| glycolide | 55 | 60 | 50 | 55 | 55 | 65 |
| Initiator Functionality | 2 | 2 | 2 | 3 | 4 | 2 |
| Tg, °C. | −12 | −9 | −17 | −15 | −13 | −1 |
| Modulus E', psi | 6710 | 19178 | 409 | 3555 | 6593 | 40070 |

The composition affects both Tg and modulus in the same manner. Higher concentration of glycolide increase Tg and modulus.

EXAMPLE 12

COPOLYMER OF ε-CAPROLACTONE/ GLYCOLIDE AT 40/60 MOLE PERCENT

The procedure describe in Example 2 is substantially reproduced, except 0.22 gm of trimethylol propane (0.80 mole/mole of total monomer) is used as an initiator. A weight loss of 3.2% is observed when the polymer is devolatilized at 110° C. under high vacuum. The I.V. of the copolymer is 2.04 dl/g in HFIP and the mole ratio of PCL/PGA is found to be 39.3/60.7 by NMR. The glass transition temperature (Tg) and the melting point (Tm) of this copolymer are found to be 1° C. and 56° C., respectively, by DSC.

The tensile properties of the compression molded films of this elastomer are summarized below:

|  | Tensile Stress | | Elongation |
| --- | --- | --- | --- |
|  | @ 300% Elong. [psi] | @ Break [psi] | @ Break [%] |
| Avg. | 1270 | 4020 | 1027 |
| S.D. | 47 | 344 | 78 |

The tensile properties of this copolymer, which is initiated with trimethylol propane, are equivalent to diethylene glycol initiated copolymer (Example 7).

EXAMPLE 13

COPOLYMER OF ε-CAPROLACTONE/ GLYCOLIDE AT 40/60 MOLE PERCENT

The procedure described in Example 2 is substantially reproduced, except 0.136 gm of pentaerythritol (0.50 mmole/mole of total monomer) is used as an initiator. A weight loss of 4.6% is observed when the polymer is devolatilized at 110° C. under high vacuum. The I.V. of the copolymer is 2.26 dl/g in HFIP and the mole ratio of PCL/PGA is found to be 34.1/65.9 by NMR. The glass transition temperature (Tg) and the melting point (Tm) of this copolymer are found to be 0° C. and 55° C., respectively, by DSC.

The tensile properties of the compression molded films of this elastomer are summarized below:

|  | Tensile Stress | | Elongation |
| --- | --- | --- | --- |
|  | @ 300% Elong. [psi] | @ Break [psi] | @ Break [%] |
| Avg. | 1529 | 3253 | 718 |
| S.D. | 24 | 665 | 133 |

The tensile properties of this copolymer, which is initiated with pentaerythritol, are slightly lower than diethylene glycol initiated copolymer (Example 7). The final composition of this copolymer is close to PCL/PLA at 35/65 by mole %.

EXAMPLE 14

COPOLYMER OF ε-CAPROLACTONE/ GLYCOLIDE/p-DIOXANONE AT 40/55/5 MOLE PERCENT

The procedure described in Example 2 is substantially reproduced with 45.66 gm (0.40 mole) of ε-caprolactone, 63.84 gm (0.55 mole) of glycolide, 5.10 gm (0.05 mole) of p-dioxanone, 0.114 ml (1.20 mmole/mole of total monomer) of distilled diethylene glycol and 0.0673 ml stannous octoate (0.33 molar solution is toluene). A weight loss of 1.6% is observed when the polymer is devolatilized at 110° C. under high vacuum. The I.V. of the copolymer is 1.51 dl/g in HFIP and the mole ratio of PCL/PGA/PDS is found to be 38.5/56.2/5.4 by NMR. The glass transition temperature (Tg) and the melting point (Tm) of this copolymer are found to be −6° C. and 54° C., respectively, by DSC.

The tensile properties of the compression molded films of this elastomer are summarized below:

|  | Tensile Stress | | Elongation |
| --- | --- | --- | --- |
|  | @ 300% Elong. [psi] | @ Break [psi] | @ Break [%] |
| Avg. | 794 | 3122 | 1243 |
| S.D. | 15 | 210 | 61 |

This copolymer also exhibits excellent elastomeric properties.

EXAMPLE 15

ABSORPTION OF ε-CAPROLACTONE/ GLYCOLIDE ELASTOMERS

The rate of absorption of ε-caprolactone/glycolide elastomers are measured by the rate of In Vitro weight loss at 50° C. in pH 7.27 phosphate buffer solution. Some of the weight loss data of the ε-caprolactone/glycolide 40/60, 45/55 and 50/50 elastomers are shown below:

| Example No. | 2 | 1 | 3 |
| --- | --- | --- | --- |
| Composition of Caprolactone/glycolide ABSORPTION | 40/60 | 45/55 | 50/50 |
| In Vitro hydrolysis 50° C./pH 7.27 phosphate buffer % weight loss |  |  |  |
| @ 49 days | 93.9 | 91.2 | 91.1 |
| @ 140 days | 99.6 | 99.1 | 99.0 |

The data from this table show that the absorption of these elastomers is very rapid. The amount of weight loss is a measure of In Vivo absorption, since synthetic polymers degrade via hydrolysis.

We claim:

1. An elastomeric suture formed from a bioabsorbable elastomer wherein the elastomer consists essentially of a random copolymer of: a) from about 35 to about 45 weight percent of a first monomer selected from the group consisting of ε-caprolactone, trimethylene carbonate, and ether lactone and combinations thereof, and b) the balance of the copolmer being substantially a second monomer selected from the group consisting of glycolide, para-dioxanone and combinations thereof, wherein the random copolymer exhibits an inherent viscosity of from about 1.0 dL/g to about 2.0 dL/g and exhibits a percent elongation greater than 500 percent.

2. The elastomeric suture of claim 1 wherein the random copolymer is a copolymer of ε-caprolactone and glycolide.

3. The elastomeric suture of claim 1 wherein the random copolymer is a copolymer of from about 40 to about 45 weight percent of ε-caprolactone, and the balance being glycolide.

4. The elastomeric suture of claim 2 wherein the bioabsorbable elastomer exhibits a modulus less than about 40,000 psi.

5. The elastomeric suture of claim 4 wherein the bioabsorbable elastomer exhibits a modulus less than about 20,000.

6. The elastomeric suture of claim 5 wherein the bioabsorbable elastomer exhibits complete bioabsorption within one year.

7. The elastomeric suture of claim 2 wherein the bioabsorbable elastomer exhibits complete bioabsorption within six months.

8. A bioabsorbable elastomer wherein the elastomer consists essentially of a random copolymer of: a) from about 40 to about 45 weight percent of a first monomer selected from the group consisting of ε-caprolactone, trimethylene carbonate, an ether lactone and combinations thereof, and b) the balance of the copolymer being substantially a second monomer selected from the group consisting of glycolide, para-dioxanone and combinations exhibiting a percent elongation of greater than 500 percent.

9. An elastomeric suture formed from a bioabsorbable elastomer wherein the elastomer consists essentially of a random copolymer of: a) from about 35 to about 45 weight percent of a first monomer selected from the group consisting of ε-caprolactone, trimethylene carbonate, an ether lactone and combinations thereof, and b) the balance of the copolymer being substantially a second monomer selected from the group consisting of glycolide, para-dioxanone and combinations thereof, wherein the random copolymer exhibits an inherent viscosity of from about 1.0 dL/g to about 2.0 dL/g and a percent elongation greater than about 500.

* * * * *